United States Patent
Maldari

(10) Patent No.: US 11,911,183 B2
(45) Date of Patent: Feb. 27, 2024

(54) IMPLANTABLE MEDICAL SYSTEM FOR MEASURING A PHYSIOLOGICAL PARAMETER

(71) Applicant: SORIN CRM SAS, Clamart (FR)

(72) Inventor: Mirko Maldari, Paris (FR)

(73) Assignee: SORIN CRM SAS, Clamart (FR)

( * ) Notice: Subject to any disclaimer, the term of this patent is extended or adjusted under 35 U.S.C. 154(b) by 86 days.

(21) Appl. No.: 17/110,045

(22) Filed: Dec. 2, 2020

(65) Prior Publication Data
US 2021/0177350 A1    Jun. 17, 2021

(30) Foreign Application Priority Data
Dec. 3, 2019   (FR) ........................................ 1913677

(51) Int. Cl.
*A61B 5/00* (2006.01)
*A61B 5/308* (2021.01)
*A61B 5/28* (2021.01)

(52) U.S. Cl.
CPC ................ *A61B 5/686* (2013.01); *A61B 5/28* (2021.01); *A61B 5/308* (2021.01)

(58) Field of Classification Search
CPC ... A61B 5/686; A61B 5/346–366; A61B 5/28; A61B 5/308
See application file for complete search history.

(56) References Cited

U.S. PATENT DOCUMENTS

| | | | |
|---|---|---|---|
| 4,686,987 A | | 8/1987 | Salo et al. |
| 5,058,583 A | * | 10/1991 | Geddes ................ A61N 1/3686 607/18 |
| 2007/0055170 A1 | | 3/2007 | Lippert et al. |
| 2007/0239218 A1 | * | 10/2007 | Carlson .............. A61N 1/39622 607/18 |
| 2008/0262365 A1 | | 10/2008 | Bjorling |
| 2013/0138008 A1 | | 5/2013 | Patangay et al. |
| 2018/0021585 A1 | | 1/2018 | An et al. |
| 2019/0111268 A1 | | 4/2019 | Christie et al. |
| 2019/0111270 A1 | * | 4/2019 | Zhou ...................... A61B 5/349 |

FOREIGN PATENT DOCUMENTS

| | | |
|---|---|---|
| JP | S52125372 A | 10/1977 |
| JP | 2006501892 A | 1/2006 |

OTHER PUBLICATIONS

Office action issued in EP Application No. 20211456.7 dated Apr. 23, 2021.
Search Report issued in FR Application No. 1913677 dated Sep. 28, 2020.

* cited by examiner

*Primary Examiner* — Scott M. Getzow

(57) ABSTRACT

An implantable medical system includes at least four electrodes forming a dipole emitter and a dipole receiver which is distinct from the dipole emitter. The system is configured to recover physiological mechanical information by way of the two dipoles, by analyzing a received and processed electrical signal, wherein the amplitude has been modulated in accordance with the electrical properties of the propagation medium between the dipole emitter and the dipole receiver. Thus, a parameter which is representative of a pre-ejection period may be extracted from the attenuation of the voltage between the dipole emitter and the dipole receiver by taking an electrocardiogram or an electrogram into account.

8 Claims, 6 Drawing Sheets

IMPLANTABLE MEDICAL SYSTEM FOR MEASURING A PHYSIOLOGICAL PARAMETER

CROSS-REFERENCE TO RELATED PATENT APPLICATIONS

This application claims the benefit of and priority to French Patent Application No. 1913677, filed Dec. 3, 2019, which is incorporated by reference herein in its entirety.

BACKGROUND

The present invention relates to an implantable medical system configured to carry out a measurement of a physiological parameter.

Impedance cardiography is a known technique for measuring physiological parameters, in particular haemodynamic parameters.

Impedance cardiography may be used for non-invasive measurements using an external device coupled to surface electrodes.

In the case of an implantable medical system, it is known that cardiographic impedance measurements are carried out by supplying current and measuring the voltage between two electrodes of the same lead. The prior art document US 2019/0111268 A concerns such a local impedance measurement between two electrodes of the same subcutaneous lead. The document US 2019/0111268 A proposes detecting a problem with the cardiac rhythm, more precisely cardiac arrhythmia, on the basis of cardiac events identified from an electrical signal.

However, it is known that problems with cardiac rhythm, such as cardiac arrhythmia, corresponding to an abnormal variation in the rhythm of the beats of the heart which affect its proper function, can be distinguished from cardiac insufficiency, which is the lack of ability of the heart to pump a sufficient quantity of blood to ensure a sufficient flow of blood throughout the body.

Cardiac insufficiency may affect only part of the heart, or all of it. Cardiac insufficiency is a chronic and progressive change, which is generally slow, which may take place over a number of years.

It has been shown that the detection of cardiac events as described in US 2019/0111268 A for identifying a cardiac rhythm problem is not suitable for monitoring cardiac insufficiency (also known as heart failure). In fact, the impedance measurement proposed in the document US 2019/0111268 A is relative to a local measurement between two electrodes of the same lead, which makes it less sensitive to pulmonary activity and to the circulation of blood in the neighboring organs. However, respiratory and haemodynamic information relating to pulmonary activity and to the circulation of blood in the neighboring organs is also information which is useful to diagnosis and to monitoring cardiac insufficiency.

Thus, the aim of the present invention is to improve and optimize the diagnosis and monitoring of cardiac insufficiency.

The aim of the present invention is achieved by means of an implantable medical system for measuring at least one physiological parameter, comprising at least one dipole emitter formed by two electrodes connected to a generator and configured in order to emit an electrical signal; at least one dipole receiver formed by two electrodes, each being distinct from the electrodes of the dipole emitter, the dipole receiver being configured to capture the electrical signal emitted by means of the dipole emitter; and an analysis module comprising at least one amplifier, an envelope detector and an analogue-to-digital converter and a processing means for processing the electrical signal captured by means of the dipole receiver; and a detection means configured to produce an electrocardiogram or an electrogram; the analysis module furthermore being configured to combine the processed electrical signal and the electrocardiogram or the electrogram in order to determine therefrom a parameter which is representative of a pre-ejection period.

The fact that the system has at least four electrodes, so that the dipole emitter is distinct from the dipole receiver, means that a more complete measurement of impedance can be obtained which is thus more representative of the surrounding medium, in particular more complete and more representative of the surrounding medium than a measurement between only two electrodes of the same lead. In fact, the present system can be used to recover physiological mechanical information by means of the two dipoles by analyzing the received and processed electrical signal the amplitude of which has been modulated as a function of the electrical properties of the propagation medium between the dipole emitter and the dipole receiver.

Thus, a parameter which is representative of a pre-ejection period may be extracted from the attenuation of the voltage between the dipole emitter and the dipole receiver by taking the electrocardiogram or the electrogram into account. The determination of the parameter which is representative of a pre-ejection period provides an indicator which is adapted to the diagnosis and monitoring of cardiac insufficiency.

SUMMARY

The present invention may be further improved by means of the following embodiments.

In accordance with one embodiment, the analysis module may be configured to extract from the processed electrical signal a variation in volume and/or a variation in pressure as a function of time proportional to a drop in voltage between the dipole emitter and the dipole receiver.

The determination of the variation in the volume of the heart and the lungs can advantageously be used to recover haemodynamic and respiratory information from the same processed electrical signal. The determination of the variation in the volume of the heart may be used to identify opening of the aortic valve.

In accordance with one embodiment, the determination of the pre-ejection period may comprise the detection of the R wave or the Q wave of a QRS complex captured by the detection means.

The onset time for the Q wave or the R wave is a parameter which is necessary in order to be able to determine the pre-ejection period.

Considering an electrocardiogram, the onset time for the Q wave may be identified from the R wave of the QRS complex because the R wave is more dominant than the Q wave (the R peak having a greater amplitude than that of the Q peak), and thus is easier to detect than the Q wave.

The detection of the R wave per se may also be used as an indicator of the onset time for the pre-ejection period and thus can be used to reduce the complexity of the analysis module of the system which is necessary for the identification of the Q wave. Detection of the R wave may be carried out from an electrocardiogram or an electrogram.

In accordance with one embodiment, the analysis module may be capable of also monitoring a parameter which is representative of the efficacy of a therapy by taking into account a parameter which is representative of a pre-ejection period.

The analysis module of the present system is thus capable of evaluating a haemodynamic parameter such as the ejection fraction or the ejection volume, which are parameters that can be used to evaluate cardiac performance. Thus, the present system is even better adapted to monitoring cardiac insufficiency and the prescribed therapy.

In accordance with one embodiment, the two electrodes of the dipole receiver may be configured to simultaneously capture the emitted electrical signal and an electrocardiogram or an electrogram.

Thus, the same electrodes may act both as detecting electrodes and as the dipole receiver. Thus, the dipole receiver has a dual function, which means that the system can be optimized, by reducing the number of electrodes which are necessary.

In accordance with one embodiment, the activation of the analysis module may be triggered by the detection of at least one peak of a PQRST complex captured by the detection means.

Thus, the energy consumption of the system may be reduced by limiting the period during which the analysis module of the system is activated. Advantageously, the analysis module may, for example, be activated during a window of time which may start from detection of at least one peak of the PQRST complex.

In accordance with one embodiment, the system may comprise a means which is capable of detecting a mechanical activity of the heart from an acoustic signal which is representative of the sounds of the heart and in which the analysis module may be configured in order to compare said acoustic signal with the processed electrical signal.

The acoustic signal can be used to reveal the mechanical activity of the cardiac valves. The analysis of the various types of signals can be used to characterize them better and to highlight information which is useful in monitoring cardiac insufficiency.

For this reason, the system is configured in order to detect and capture the acoustic activity of the heart. The information relative to the acoustic activity that is thus captured may be used in order to correlate the processed electrical signal captured by the analysis module of the system.

In accordance with one embodiment, the system may comprise a first implantable medical device provided with the dipole emitter, and a second implantable medical device which is distinct from the first implantable medical device and is provided with the dipole receiver.

Thus, it is possible to obtain a measurement of impedance which is more complete and thus is more representative of the surrounding medium, in particular more complete and more representative of the surrounding medium than a measurement between only two electrodes of the same lead. In fact, the dipoles are coupled together galvanically and an electric field is propagated through the human body from the dipole emitter to the dipole receiver. The electrical signal received by the dipole receiver is then modulated in amplitude. By demodulating the received signal, it is possible to recover at least one physiological parameter from which a parameter which is representative of a pre-ejection period may be defined.

In accordance with one embodiment, one of the first implantable medical device or the second implantable medical device may be a subcutaneous implantable cardioverter defibrillator or an event recorder; and the other of the first implantable medical device or the second implantable medical device may be an implantable endocardial device.

Thus, the electric field emitted by the dipole emitter is propagated through a channel which can recover both haemodynamic and respiratory information. The present implantable medical system for measuring at least one physiological parameter is therefore configured in order to use pre-existing implantable medical devices, i.e. devices which have a supplemental function in addition to the determination of a parameter which is representative of a pre-ejection period, such as a defibrillation function.

In accordance with one embodiment, the implantable endocardial device may be a leadless cardiac pacemaker.

A leadless cardiac pacemaker can be used to make an implantation procedure less invasive than implantable devices with a lead. Thus, a leadless cardiac pacemaker can be used to avoid complications linked to transvenous lead and to the subcutaneous pulse generator used in conventional cardiac pacemakers.

BRIEF DESCRIPTION OF THE DRAWINGS

The invention and its advantages will now be explained in more detail below by means of preferred embodiments, in particular made with reference to the accompanying figures, in which.

DETAILED DESCRIPTION

The invention will now be described in more detail using advantageous embodiments by way of example and with reference to the figures. The embodiments described are simply configurations which are possible and it should be borne in mind that the individual features as described above may be provided independently of each other or may be omitted altogether when carrying out the present invention.

Figure 1:
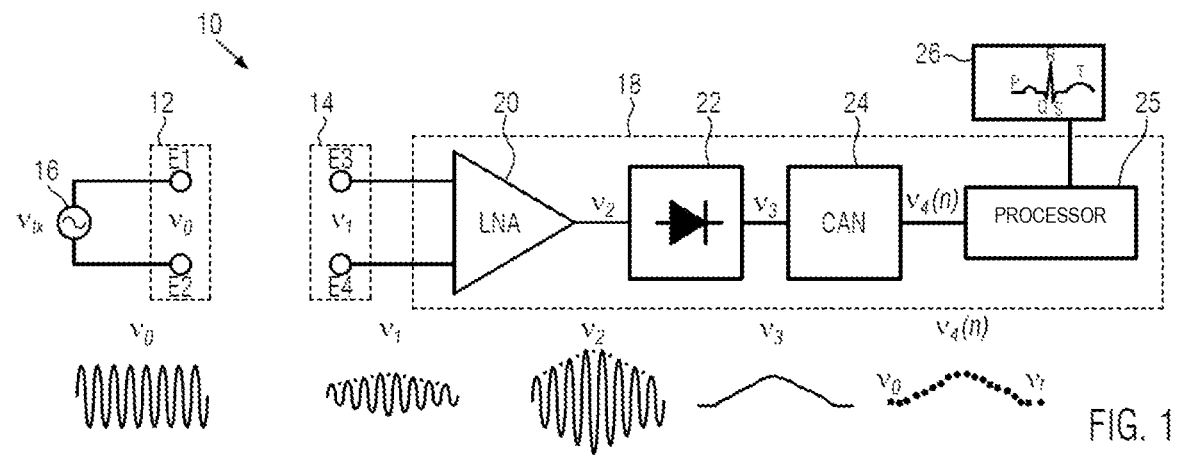
FIG. 1 represents a diagrammatic view of an implantable medical system in accordance with the present invention.

FIG. 1 illustrates an implantable medical system 10 in accordance with the present invention. In addition, the lower portion of FIG. 1 illustrates electrical signals $V_0$ to $V_4$.

The implantable medical system 10 in accordance with the present invention comprises a dipole emitter 12 and a dipole receiver 14. The dipole emitter 12 is formed by a pair of electrodes E1, E2. The dipole receiver 14 is formed by a pair of electrodes E3, E4. The electrodes E1, E2 are distinct from the electrodes E3, E4.

The two electrodes E1, E2 of the dipole emitter 12 are connected to a generator 16 which is configured to generate an electrical input signal $V_0$ at a defined frequency $f_0$. It should be noted that the frequency $f_0$ must be sufficiently high not to stimulate the heart of a patient by interfering with the normal cardiac activity of the patient. In particular, the defined frequency $f_0$ is more than 1 kHz; in particular, it may be more than 10 kHz. The generator 16 may be a voltage or current generator.

The implantable medical system 10 also comprises an analysis module 18. The analysis module 18 comprises an amplifier 20, in particular a low noise band pass amplifier which can be used to amplify the signal $V_1$ at the frequency $f_0$.

The amplifier 20 may comprise an analogue filter.

In a variation, the amplifier 20 may be constituted by a plurality of low noise amplifiers. In this variation, the selection of one of the low noise amplifiers is made as a function of the mutual position of the dipole emitter 12 and of the dipole receiver 14 which affects the attenuation of the electrical signal. In this manner, the energy consumption of the system 10 may be optimized by activating only the low noise amplifier necessary for providing sufficient detection of the electrical signal for the measurement, i.e. which satisfies a certain predefined signal-to-noise ratio.

In another variation, the amplifier 20 may be a variable gain amplifier and/or a programmable gain amplifier.

The analysis module 18 furthermore comprises an envelope detector 22 and an analogue-to-digital converter 24 which are configured for processing an electrical signal captured by means of the dipole receiver 14.

The analysis module 18 additionally comprises a processing means 25. The processing means 25 is a processor 25. The processor 25 may comprise a digital filter means in order to digitally process the electrical signal $V_4$. In a variation, the digital filter means is disposed between the analogue-to-digital converter 24 and the processor 25.

The processor 25 is connected to a detection means 26 which is configured to produce an electrocardiogram or an electrogram.

In one embodiment in which the detection means 26 is a subcutaneous device such as an implantable subcutaneous defibrillator or an implantable loop recorder, the detection means 26 is configured to produce an electrocardiogram, in particular a subcutaneous electrocardiogram. Thus, the detection means 26 is capable of detecting a PQRST complex, and in particular the P, Q and R waves.

In another embodiment in which the detection means 26 is an implantable endocardial device such as an implantable leadless cardiac pacemaker in the form of a capsule, the detection means 26 is configured to produce an electrogram. Thus, the detection means 26 is capable of detecting the R wave from a local measurement of the depolarization of the right ventricle. Activation of the analysis module 18 may be triggered by signals from the detection means 26, in particular by detection of the R wave in order to optimize the operating duration of the active components of the analysis module 18 and thus to reduce the required energy consumption of the system 10.

In order to further reduce the energy consumption of the system 10, the measurement of the parameter which represents a pre-ejection period may be carried out only during a predetermined window of time, at regular intervals. The frequency of the measurement intervals may also be reduced in order to save energy.

The two electrodes E3, E4 of the dipole receiver 14 may be configured to capture the electrical signal at the same time.

In a variation, the two electrodes E3, E4 of the dipole receiver 14 are configured to capture the emitted electrical signal and the electrocardiogram at the same time.

The processor 25 of the analysis module 18 is further configured to combine the processed electrical signal and the electrocardiogram in order to determine a parameter which is representative of a pre-ejection period therefrom.

The operation of the implantable medical system 10 is explained in more detail below by using the electrical signals $V_0$ to $V_4$ illustrated in FIG. 1. FIG. 1 illustrates an electrical input signal $V_0$ with a fixed amplitude. In a variation, the electrical input signal $V_0$ may have a variable amplitude in order to improve the signal-to-noise ratio.

In another variation, the amplitude of the electrical input signal $V_0$ may be adjusted from the feed-back from the dipole receiver 14 which, in this variation, is furthermore configured for transmission via telemetry with a third party device, for example an external device.

The dipole receiver 14 captures an electrical signal $V_1$ which differs from $V_0$ because the electric field has been propagated, following application of the electrical signal $V_0$, through a volume, also termed a channel, for example human tissue, for which the impedance is non-zero.

The electrical signal $V_1$ is then amplified by means of the amplifier 20, resulting in an amplified electrical signal $V_2$. The envelope of the electrical signal $V_2$, represented by the signal $V_3$, is determined by means of the envelope detector 22, in particular by an amplitude demodulation of the electrical signal $V_2$. The envelope of the electrical signal $V_3$ is then sampled by the analogue-to-digital converter 24 in a manner such as to obtain a digital signal $V_4(n)$ in which n represents the number of samples.

The digital signal $V_4$ may be processed by means of the processor 25 and digitally filtered further in order to distinguish the respiratory information from the haemodynamic information recovered from the processed electrical signal.

It should be noted that the cutoff frequency of the filters may be adjusted as a function of the characteristics of each physiological parameter to be determined. As an example, a low pass filter with a cutoff frequency $f_c$ in the range $f_c=0.5$ Hz to 5 Hz, in particular $f_c=1$ Hz, is used to isolate respiratory signals, while a band pass filter with $f_{c1}=1$ Hz and $f_{c2}=30$ Hz is used to isolate haemodynamic signals from the processed electrical signal $V_4$.

From the processed electrical signal, the analysis module 18 is configured to extract therefrom a variation in volume and/or a variation in pressure as a function of time which is proportional to a reduction in the voltage between the dipole emitter 12 and the dipole receiver 14.

Figure 2:
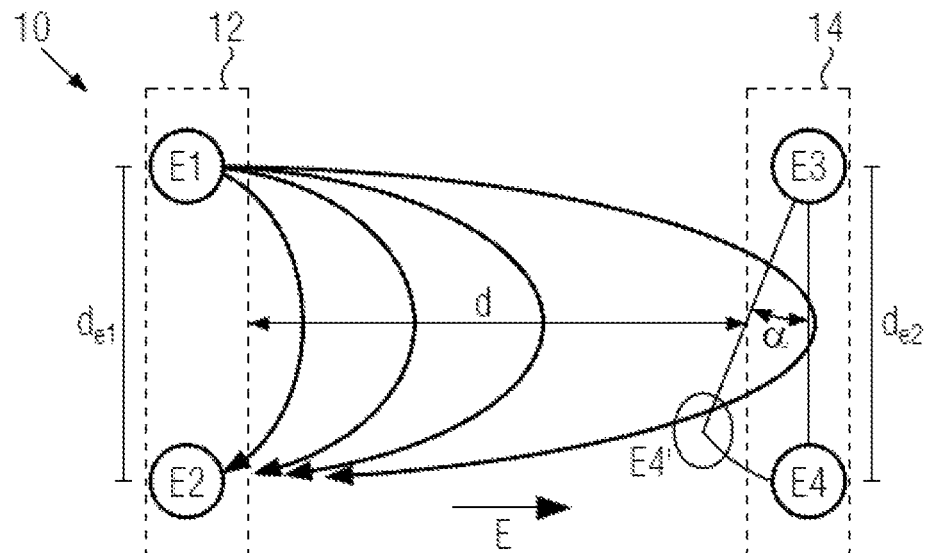
FIG. 2 represents a diagrammatic view of the propagation of an electrical signal between a dipole emitter and a dipole receiver in accordance with the present invention.

FIG. 2 diagrammatically illustrates the propagation of an electrical signal $V_0$ from the dipole emitter 12 formed by the pair of electrodes E1, E2 up to the dipole receiver 14 formed by the pair of electrodes E3, E4 of the implantable medical system 10 in accordance with the present invention.

The elements with the same reference numerals already used for the description of FIG. 1 will not be described again in detail; reference should be made to their descriptions above.

In the implanted state of the device and by applying the signal $V_0$, the dipole emitter 12 is used to generate an electric field E propagating through the tissues of a human body to the dipole receiver 14. The dipole receiver 14 detects a potential difference which depends on the electric field E, illustrated in FIG. 2 by the electrical signal $V_1$. The electrical signal $V_1$ which is detected principally depends on four factors, which are: the length "d" of the propagation channel, i.e. the distance between the dipole emitter 12 and the dipole receiver 14; the orientation "a" of the dipoles 12, 14 with respect to each other; the inter-electrode distances "$d_{e1}$" and "$d_{e2}$" for the dipoles 12, 14, i.e. the distance between the electrodes E1, E2 and the distance between the electrodes E3, E4; and the electrical properties of the propagation medium.

As can be seen in FIG. 2, the electrodes E3, E4 form a dipole receiver the orientation of which differs from that of the dipole receiver formed by the electrodes E3, E4'. The difference in orientation between the dipoles E3, E4 and E3, E4' is illustrated by the angle α in FIG. 2. When the implantable medical system 10 is implanted in a human body, in particular in or in the vicinity of the heart, the electrical signal $V_1$ of the dipole receiver 14 is modulated in amplitude. This results from the fact that respiration changes the properties of the environment, in particular the quantity of oxygen present in the lungs, which causes the attenuation of the electrical signal to vary during its transmission along the propagation channel, and thus causes a variation in the amplitude of the electrical signal $V_1$.

Figure 3:
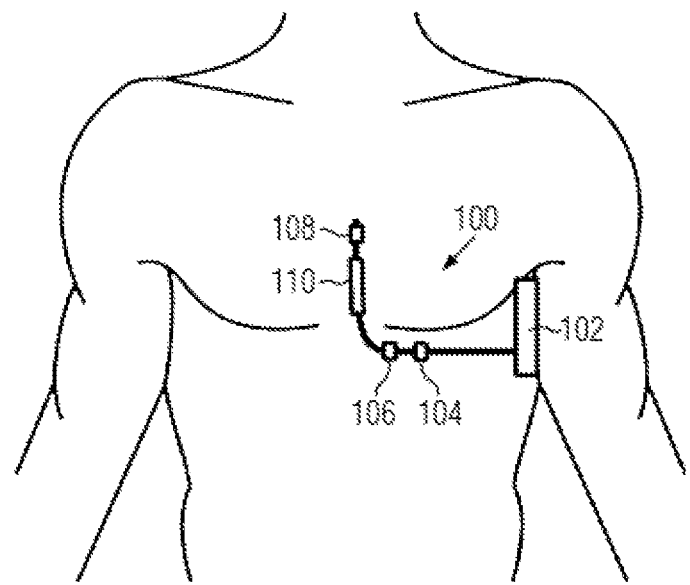
FIG. 3 represents the integration of the implantable medical system in accordance with the present invention into a subcutaneous implantable device.

In accordance with a second embodiment, FIG. 3 represents the integration of the implantable medical system 10 in accordance with the present invention into an implanted device 100, in this case an implantable subcutaneous defibrillator. In a variation, the device 100 is an event recorder, for example an implantable loop recorder.

The implantable subcutaneous device 100 as shown in FIG. 3 comprises a housing 102, three electrodes 104, 106, 108 and a defibrillation electrode 110. The housing 102 of the implantable subcutaneous device 100 may comprise a telemetry module (not shown).

The implantable subcutaneous device 100 is suitable for integrating the implantable medical system 10 in accordance with the present invention, because it comprises at least a dipole emitter and a dipole receiver wherein the electrodes of each dipole are distinct from each other. Table 1 below lists configurations of the dipole emitters and dipole receivers which may be used in the implantable subcutaneous device 100 in order to operate the system 10 in accordance with the present invention.

TABLE 1

| # | Dipole emitter | Dipole receiver |
|---|---|---|
| 1 | 104-106 | 108-102 |
| 2 | 104-108 | 106-102 |
| 3 | 110-106 | 108-102 |
| 4 | 110-108 | 106-102 |
| 5 | 104-102 | 106-108 |
| 6 | 104-102 | 110-106 |
| 7 | 104-102 | 110-108 |
| 8 | 110-102 | 106-108 |
| 9 | 110-102 | 104-106 |
| 10 | 110-102 | 104-108 |

TABLE 1-continued

| # | Dipole emitter | Dipole receiver |
|---|---|---|
| 11 | 108-102 | 104-106 |
| 12 | 106-102 | 104-108 |
| 13 | 108-102 | 110-106 |
| 14 | 106-102 | 110-108 |
| 15 | 106-108 | 104-102 |
| 16 | 110-106 | 104-102 |
| 17 | 108-102 | 104-102 |
| 18 | 106-108 | 110-102 |
| 19 | 104-106 | 110-102 |
| 20 | 104-108 | 110-102 |

As indicated in Table 1, one of the electrodes may be constituted by the housing 102 of the device 100. Any of the combinations of electrodes may be used, including the defibrillation electrode 110.

The implantable subcutaneous device 100 may also comprise a detection means formed by at least one pair of electrodes from those listed in Table 1, configured in order to produce a subcutaneous electrocardiogram from which a PQRST complex can be detected. Thus, the R and Q waves in particular are identifiable from the PQRST complex.

Thus, the system 10 in accordance with the present invention may be implemented by means of a pre-existing device. In addition, a practitioner may advantageously select the configuration of the dipole emitter and the dipole receiver which is the most suitable for the physiological parameters that are to be captured.

In a variation, the system 10 comprises an accelerometer integrated into the implantable subcutaneous device 100, which can be used to detect a mechanical activity of the heart. The mechanical activity of the heart may be compared with the captured electrical signal in order to establish a correlation between the signals.

Figure 4:
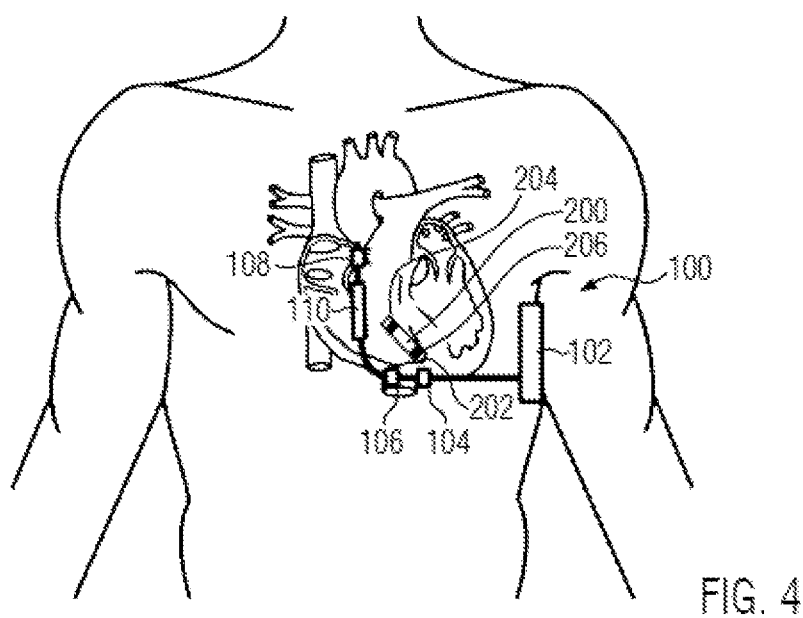
FIG. 4 represents the integration of the implantable medical system in accordance with the present invention into a multi-device system.

In accordance with a third embodiment, FIG. 4 represents the integration of the implantable medical system 10 in accordance with the present invention into a multi-device system 100, 200. The multi-device system 100, 200 shown in FIG. 4 comprises an implantable subcutaneous device 100 in accordance with the second embodiment and an endocardial device, such as a cardiac pacemaker, in particular a leadless pacemaker 200.

The elements with the same reference numerals already used for the description of FIG. 3 will not be described again in detail; reference should be made to their descriptions above.

In a variation, an event recorder or an implantable loop recorder could be used in place of the implantable subcutaneous device 100. An event recorder or implantable loop recorder of this type may comprise a detection means, formed by at least one pair of electrodes of said recorder, and configured to produce a subcutaneous electrocardiogram from which a PQRST complex could be detected. Thus, the R and Q waves in particular are identifiable from the PQRST complex.

The leadless pacemaker 200 comprises a tip electrode 202 disposed at one end of the leadless pacemaker 200, a first ring electrode 204 and a second annular electrode 206. The electrodes 202, 204 or 202, 206 or 204, 206 may form a dipole receiver or a dipole emitter. The leadless pacemaker 200 may comprise a telemetry module (not shown).

The leadless pacemaker 200 may furthermore comprise a detection means, formed by a pair of electrodes comprising two of the electrodes 202, 204, 206 and configured to produce an electrogram from which the R wave may be detected.

The implantable subcutaneous device 100 and the leadless cardiac pacemaker 200 each comprises electrodes which may act as the dipole receiver and dipole emitter. Thus, both the implantable subcutaneous device 100 and also the leadless cardiac pacemaker 200 may act as an emitter or receiver in the implantable system 10 of the present invention.

The implantation of the implantable subcutaneous device 100 and of the leadless cardiac pacemaker 200 as illustrated in FIG. 4 is adapted for a trans-thoracic measurement and can be used to detect changes in the volume of a chamber of the heart other than that in which the leadless cardiac pacemaker 200 is implanted.

As an example, by using the implantable subcutaneous device 100 as the emitter and the leadless cardiac pacemaker 200 implanted in the right ventricle as the receiver, information relative to the contraction of the atrium ("atrial kick") may be recovered by the leadless cardiac pacemaker 200, given that the mechanical activity of the atrium modifies both the quantity of blood present in the right ventricle and the orientation of the leadless cardiac pacemaker 200. The information relative to the contraction of the atrium may be used by the leadless cardiac pacemaker 200 in order to adapt the stimulation to the normal activity of the atrium.

In addition, because the system 10 has at least four electrodes such that the dipole emitter is distinct from the dipole receiver, it is possible to obtain a measurement of the impedance which is more complete and thus more representative of the surrounding medium than a measurement between only two electrodes of the same lead.

Furthermore, the two devices 100, 200 are configured in order to integrate the dipole emitters and dipole receivers: each of the devices 100, 200 may therefore act as the emitter and also as the receiver, depending on the practitioner's requirements. Thus, it is possible to select the configuration of the dipoles which is the most sensitive and/or the most energy-saving, in particular during the lifetime of a patient in whom the devices 100, 200 are implanted. This selection may be carried out in real time using a telemetry module.

In a variation, the implantable medical system of the present invention may be integrated into a multi-device system comprising an implantable subcutaneous device such as the device 100 and two leadless pacemakers, each being of the type of pacemaker 200 (one provided for implantation in the right ventricle and the other in the right atrium), each of the implantable subcutaneous device and the leadless pacemakers comprising at least one dipole emitter and/or receiver electrode. A system of this type is suitable for a trans-thoracic measurement and can be used to detect the changes in volume observed in the right ventricle and in the right atrium. A system of this type can thus be used to provide a more exhaustive view of the trans-thoracic measurement. Furthermore, one of the two leadless pacemakers is adapted to stimulate the heart in the right atrium. In an alternative to this variation, one of the two leadless pacemakers is provided for implantation in the left ventricle, instead of the right atrium. The fact that one pacemaker is implanted in the left ventricle and the other is implanted in the right ventricle renders inter-ventricular resynchronization to be carried out.

In another variation, the implantable medical system of the present invention may be integrated into a multi-device system comprising an implantable subcutaneous device such as the device 100 and three leadless pacemakers, each like the pacemaker 200 (one is provided for implantation in the right ventricle, another in the right atrium and yet another in the left ventricle), each of the implantable subcutaneous device and the leadless pacemakers comprising at least one dipole emitter and/or receiver electrode. A system of this type constitutes an implantable Cardiac Resynchronization Therapy (CRT) system known as a "triple chamber" system (right ventricle, right atrium and left ventricle) which is not only suitable for diagnosis, but also for the treatment of cardiac insufficiency (also known as heart failure). In fact, an implantable cardiac resynchronization system needs a leadless pacemaker for stimulation in the left ventricle in order to synchronize intra-ventricular and interventricular contraction.

Figure 5:
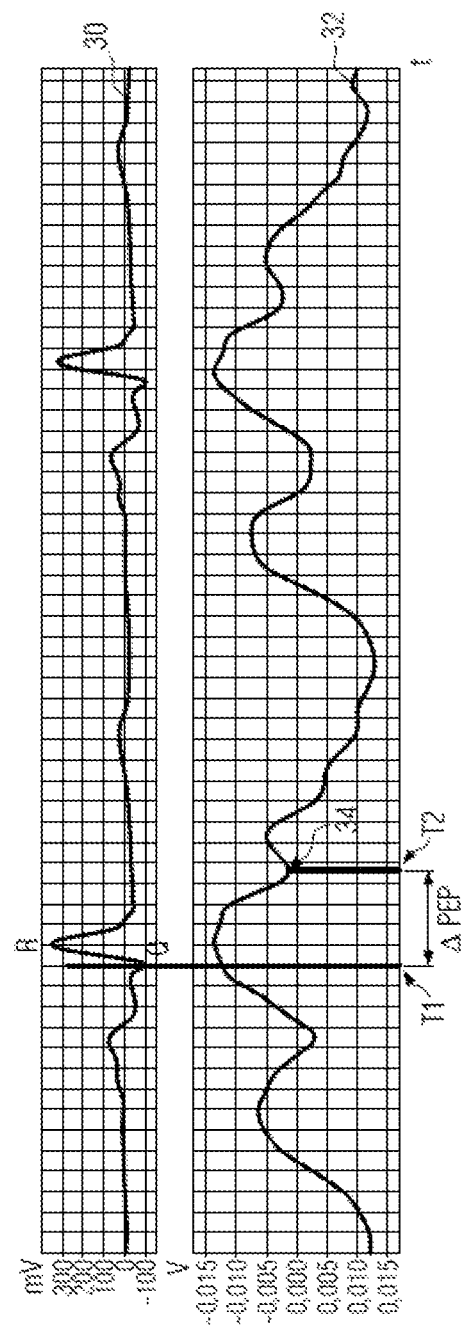
FIG. 5 represents an electrocardiogram and a processed electrical signal obtained by the implantable medical system in accordance with the present invention integrated into the multi-device system of FIG. 4.

FIG. 5 illustrates an electrocardiogram 30 and a processed electrical signal 32. The electrocardiogram 30 is captured by the generator 16 and an electrical signal is captured and processed by the analysis module 18 of the system 10 integrated into the multi-device system 100, 200, as can be seen in FIG. 4.

The elements with the same reference numerals already used for the description of FIGS. 1 to 4 will not be described again in detail; reference should be made to their descriptions above.

The analysis module 18, in particular the processor 25, is configured to combine the processed electrical signal 32 and the electrocardiogram 30 in order to determine therefrom a parameter which is representative of a pre-ejection period.

In haemodynamics, the pre-ejection period corresponds to the isovolumetric contraction which precedes systolic ejection. It is under the dependency of the sympathetic nervous system and reflects myocardial contractility.

A pre-ejection period is defined as the duration between the onset of the QRS complex, i.e. a Q wave or R wave, and opening of the aortic valve.

The electrocardiogram 30, shown in FIG. 5, can be used to identify the peak of the Q wave from the R peak of the PQRST complex. In fact, the R peak is easier to detect than the peak of the Q wave because the R peak has a larger amplitude than the Q peak.

Thus, identification of the Q peak, indicated by the reference T1 in FIG. 5, can be used to determine the onset of the pre-ejection period.

In a variation, the detection of the R wave is used as is as an indicator of the onset time for the pre-ejection period, which means that the complexity of the analysis module 18 of the system 10 necessary for the identification of the Q wave can be reduced.

In another variation, detection of the R wave is carried out from an electrogram.

The opening of the aortic valve is determined by means of the processed electrical signal 32 which has been processed by the analysis module 18 of the system 10. The processed electrical signal 32 has been digitized by means of the analogue-to-digital converter 24 of the system 10 and digitally filtered in order to distinguish respiratory information from haemodynamic information comprised in the electrical signal. A 0.5 Hz to 30 Hz band pass filter is used to recover the haemodynamic information, while a low pass filter, preferably with a cutoff frequency $f_c$ in the range 0.5 Hz and 5 Hz, in particular $f_c=1$ Hz, is used to recover the respiratory information. The range of frequencies of 0.5 Hz to 30 Hz of the band pass filter can be used both to filter the respiratory artefact by cutting out frequencies below 0.5 Hz and to filter high frequency noise, i.e. noise with a frequency of more than 30 Hz.

In a variation, when an adjustment of the frequencies is necessary, the values for the frequencies for the band pass filter and low pass filters are adjusted by means of the processor 25.

The person skilled in the art will understand that the respiratory information is relative to a change in the volume of the lungs, causing a modification to the propagation of the electric field which is in turn detected by the dipole receiver.

As illustrated in FIG. 5, it has been shown that opening of the aortic valve indicated by T2 corresponds to the first local minimum 34 of the processed electrical signal 32 following the onset of the Q wave, i.e. from T1.

Figure 6:
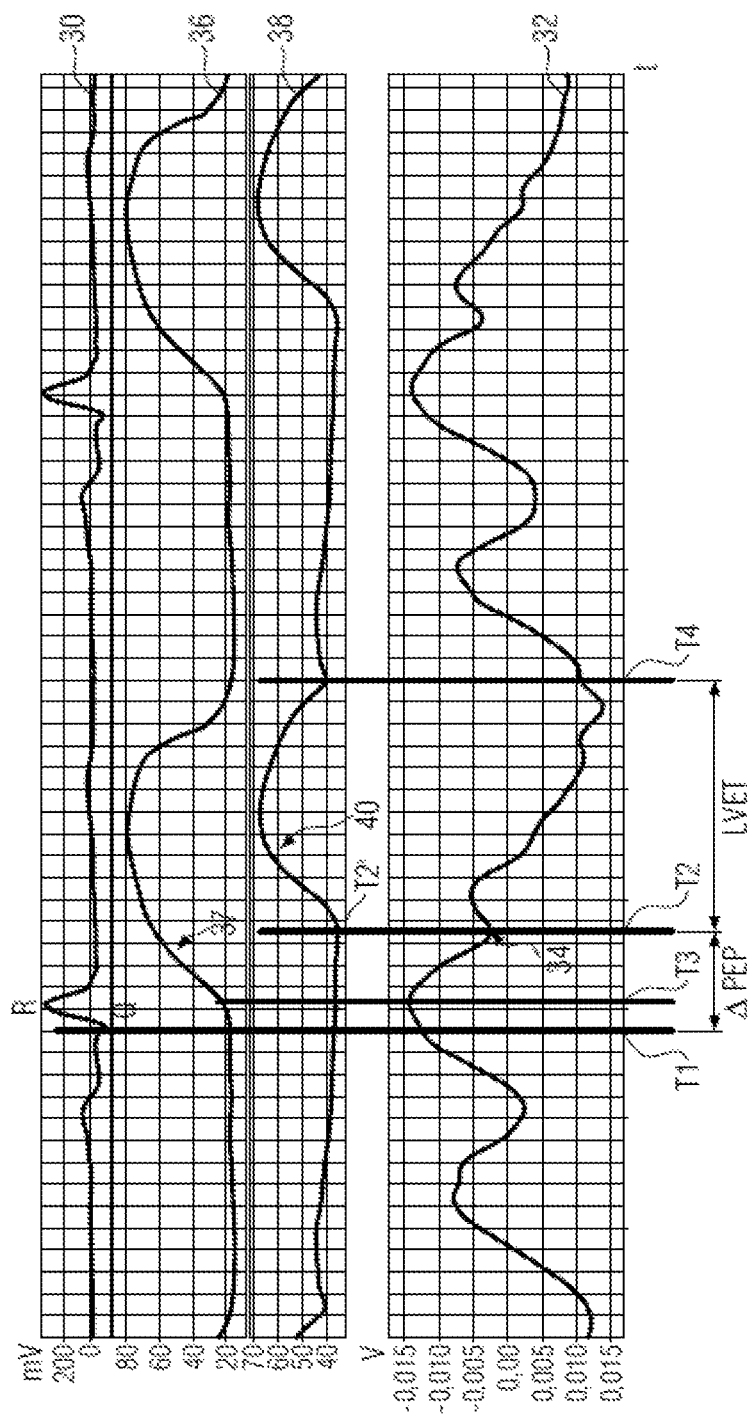
FIG. 6 shows a correlation between the processed electrical signal obtained by the implantable medical system in accordance with the present invention integrated into the multi-device system of FIG. 4 and graphs representing the pressure variations in the left ventricle and the aorta.

For this reason, the duration between the onset of the Q wave detected by means of the electrocardiogram 30 and opening of the aortic valve detected by means of the processed electrical signal 32, i.e. the duration between T1 and T2, can be used to determine the pre-ejection period indicated in FIG. 6 by the reference ΔPEP. T2 therefore corresponds to the onset time for ejection.

The duration of the pre-ejection period ΔPEP may act as an indicator when monitoring cardiac insufficiency. As an example, the higher the pre-ejection period ΔPEP is, the less the heart is assumed to be functioning efficiently.

The system 10 of the present invention can in particular be used to overcome difficulties encountered in the determination of the end of the pre-ejection period by means of prior art methods which are known to the person skilled in the art.

In a variation, the analysis module 18 is also capable, from the processed electrical signal 32, of monitoring a parameter which is representative of the efficacy of a therapy, such as the ejection fraction or the ejection volume, by taking into account the change in the measured pre-ejection period ΔPEP over a long period, in particular a period of a few weeks, months or years. To this end, the values for the measured pre-ejection periods ΔPEP may be transferred to an external device by means of a telemetry module of the system 10. In a variation, the values for the pre-ejection periods ΔPEP which are measured may be recorded on a storage means, for example a storage means of one of the devices 100, 200 of the system 10.

In another variation, the system 10 is capable of detecting a mechanical activity of the heart from an acoustic signal which is representative of the sounds from the heart. The analysis module 18 is then configured in order to compare said acoustic signal with the processed electrical signal. In yet another variation, the system 10 comprises an accelerometer, for example integrated into the implantable subcutaneous device 100, which can be used to detect a mechanical activity of the heart.

For this reason, the system 10 may be configured in order to detect and capture the mechanical/acoustic activity of the heart. The information which is captured in this manner regarding the mechanical/acoustic activity may be used to correlate the processed electrical signal 32 captured by the analysis module 18 of the system 10.

FIG. 6 represents the comparison between variations in aortic pressure and left ventricular pressure and the captured and processed electrical signal 32 represented in FIG. 5.

The elements with the same reference numerals already used for the description of FIGS. 1 to 5 will not be described again in detail; reference should be made to their descriptions above.

The variations in left ventricular pressure, represented by the plot 36 of FIG. 6, and the variations in aortic pressure, represented by the plot 38 in FIG. 6, were acquired by means of two intraventricular Millar pressure catheters placed in the aorta and in the left ventricle, in accordance with a method which is known by the person skilled in the art.

In FIG. 6, T3 indicates the onset of contraction of the ventricle. In fact, as shown by reference numeral 37 on the plot 36 of FIG. 6, beyond T3, the pressure in the left ventricle is increasing.

As shown by reference numeral 40 on the plot 38 of FIG. 6, beyond T2', the aortic pressure increases when blood circulates in the artery.

After depolarization of the ventricles represented by the QRS complex of the electrocardiogram 30, the cardiac muscle contracts, increasing the pressure of the left ventricle, as can be seen at time T4 on the plot 36. The pressure increases until it reaches a value which is sufficient to open the aortic valve at time T2'. The time comprised between T4 and T2' represents the duration of the isovolumetric contraction of the heart, which is thus termed because the blood volume in the chambers does not change (the valves are not yet open). At T2', the aortic valve opens, allowing the blood to circulate through the aorta, thereby increasing the pressure of the artery, as can be seen in plot 38 of FIG. 6, indicated by the reference numeral 40.

The variation in the aortic pressure 40 is then used to measure the time T2' corresponding to the onset of an ejection.

As can be seen in FIG. 6, the processed electrical signal 32 in accordance with the invention has a first local minimum 34 which essentially corresponds to the onset of the increase in the aortic pressure 40 at T2' of the plot 38.

FIG. 6 shows that T2'=T2, i.e. that the abscissa of the observed local minimum on the processed electrical signal 32 may be attributed to the time of opening of the aortic valve.

The variation in aortic pressure 40 may also be used to determine the duration of left ventricular ejection, indicated in FIG. 6 by the reference LVET, for "left ventricular ejection time", which corresponds to the period between T2' and T4.

Figure 7:
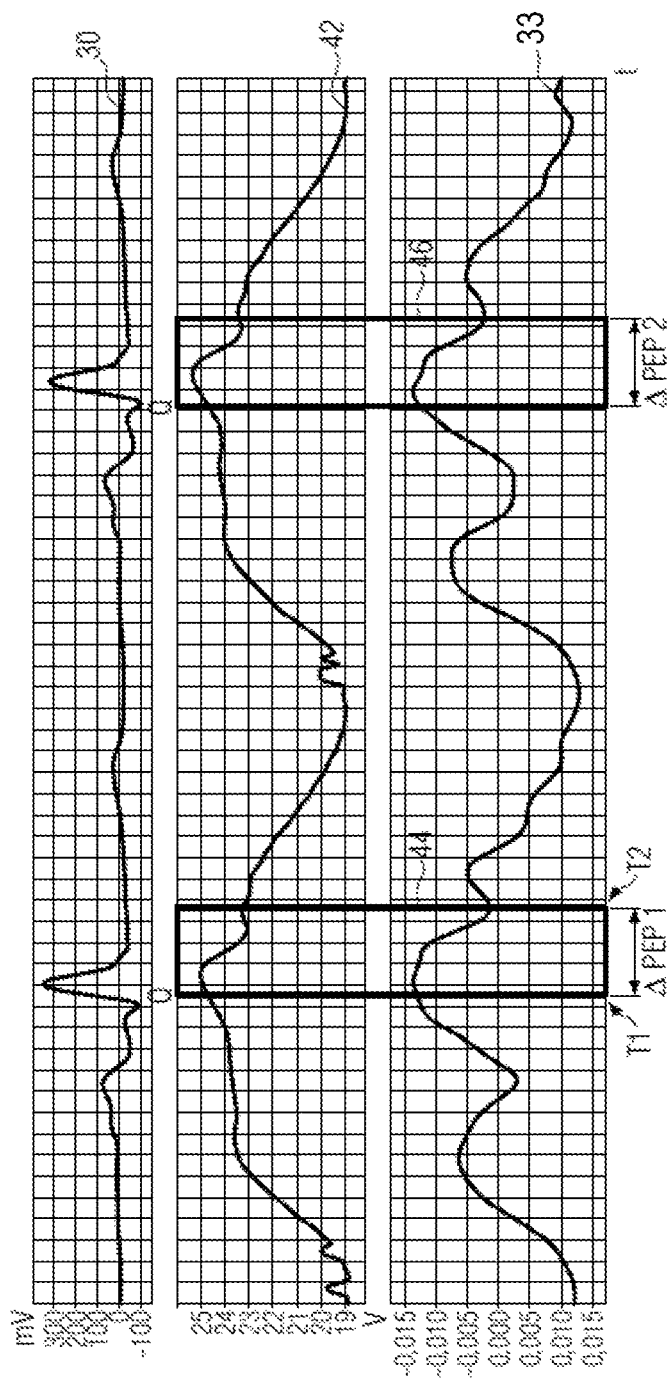
FIG. 7 shows a correlation between the processed electrical signal obtained by the implantable medical system in accordance with the present invention integrated into the multi-device system of FIG. 4 and a graph representing the variations in volume of the left ventricle.

FIG. 7 represents the comparison between the variation in volume of the left ventricle determined from a sonometric measurement and an electrical signal captured and processed by the analysis module 18 of the system 10 integrated into the multi-device system 100, 200, as can be seen in FIG. 4.

The elements with the same reference numerals already used for the description of FIGS. 1 to 6 will not be described again in detail; reference should be made to their descriptions above.

The variation in the left ventricular volume, indicated by the plot 42 in FIG. 7, was determined by means of a sonometric measurement in accordance with a method known to the person skilled in the art.

The comparison of plot 33 and plot 42 of FIG. 7 shows that the peaks, in particular the peaks included in the intervals 44 and 46, as well as the period of the signals, in particular the pre-ejection periods $\Delta PEP_1$ and $\Delta PEP_2$, are preserved from one plot to the other. In addition, the plots 33 and 42 in FIG. 7 proves that the motifs are repetitive, such as the repetition of the intervals 44 and 46. For this reason, the processed electrical signal 32 has a variation which is similar to that of the volume of the left ventricle represented by the plot 42, thereby illustrating the correlation between the processed electrical signal and the haemodynamic properties of the heart.

Figure 8:
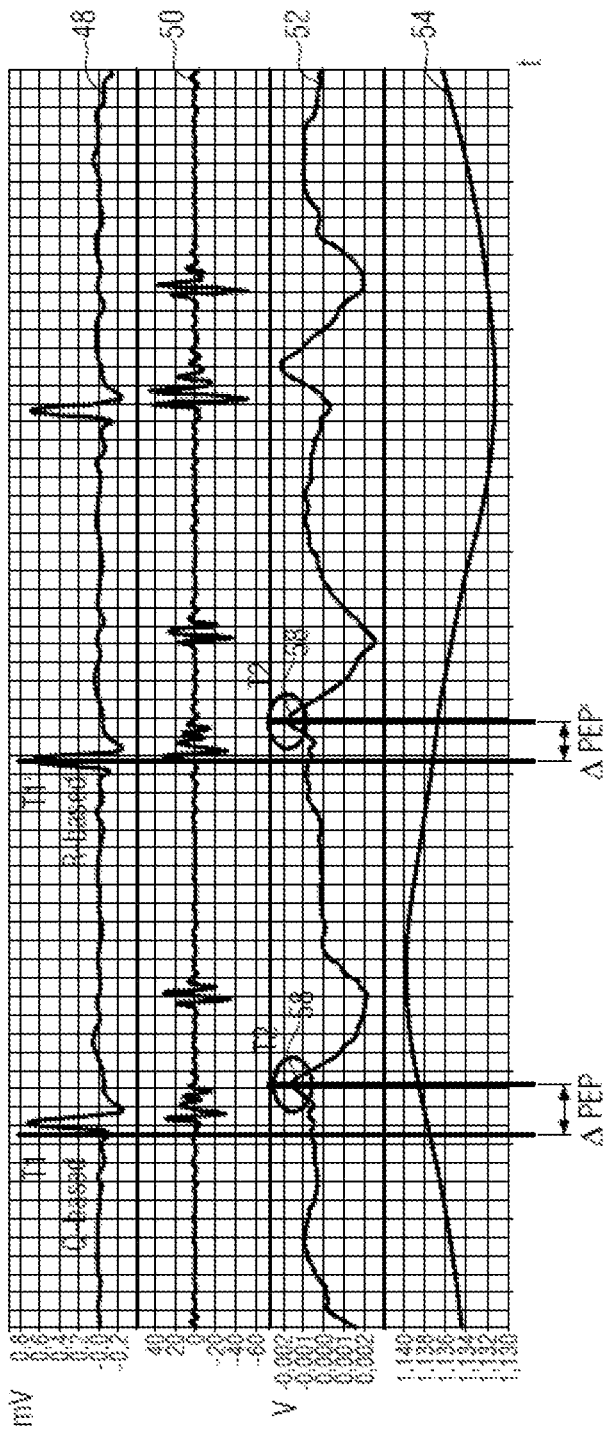
FIG. 8 represents an electrocardiogram, a phonocardiogram, and electrical signals obtained by the implantable medical system in accordance with the present invention integrated into the subcutaneously implantable device of FIG. 3.

FIG. 8 illustrates an electrocardiogram 48, a phonocardiogram 50, an electrical signal 52, a respiratory signal 54 and a haemodynamic signal 56.

The elements with the same reference numerals already used for the description of FIGS. 1 to 7 will not be described again in detail; reference should be made to their descriptions above.

The electrical signal 52 is an electrical signal captured by the analysis module 18 of the system 10 integrated into the implantable subcutaneous device 100, as can be seen in FIG. 3.

The electrical signal 52 represented in FIG. 8 is a raw signal, i.e. it has not yet been digitally processed by a filter provided for this purpose, as described with reference to FIG. 1.

The phonocardiogram 50 represented in FIG. 8 was determined by means of an acoustic measurement in accordance with a method known to the person skilled in the art.

In one embodiment, the system 10 may comprise acoustic measuring means which are suitable for capturing a phonocardiogram. In a variation, the system 10 may comprise an accelerometer. Thus, the system 10 may be configured in order to detect and capture the mechanical/acoustic activity of the heart. The information captured in this manner relating to the mechanical/acoustic activity may be used to correlate the electrical signal 52 captured by the analysis module 18 of the system 10.

The respiratory signal 54 and the haemodynamic signal 56 have been extracted from the electrical signal 52 and distinguished by digital processing. In particular, a 1 Hz to 30 Hz band pass filter is used to recover haemodynamic information, while a low pass filter, in particular with a cutoff frequency $f_c$ in the range 0.5 Hz and 5 Hz, in particular $f_c$=1 Hz, is used to recover respiratory information from the electrical signal 52.

As was explained with reference to FIGS. 5 to 7, the electrocardiogram 48 can be used to determine the onset of a pre-ejection period.

The time T1 of FIG. 8 corresponds to the onset time of a pre-ejection period determined from detection of a Q wave, T1 corresponding to the peak Q.

The time T1' of FIG. 8 corresponds to the onset time of a pre-ejection period determined from detection of an R wave, T1' corresponding to the peak R.

T1 and T1' can thus each indicate the onset of the pre-ejection period.

FIG. 8 can be used to compare the haemodynamic signal 56 captured, processed and extracted from the system 100 with the signal from the phonocardiogram 50 and to thereby illustrate the correlation between these two signals 50, 52.

As can be seen in FIG. 8, it has been shown that opening of the aortic valve indicated by T2 corresponds to the second local maximum 58 of the haemodynamic signal 56 following the onset of the Q wave or R wave, i.e. respectively from T1 or T1'.

Thus, a pre-ejection period ΔPEP determined from the Q wave of FIG. 8 corresponds to ΔPEP=T2−T1.

A pre-ejection period ΔPEP' determined from the R wave of FIG. 8 corresponds to ΔPEP'=T2−T1'.

The duration of the pre-ejection period ΔPEP may therefore be determined from the implantable subcutaneous device 100 and may act as an indicator during monitoring of cardiac insufficiency.

The present system therefore provides a simplified means for recovering information, both respiratory and haemodynamic, in order to determine a parameter which is representative of a pre-ejection period. Thus, the present system can be used to determine a pre-ejection period without it being necessary to resort to cardiac sound sensors, from which the detection of a pre-ejection period is difficult, in particular because of the high signal/noise ratio in the signal obtained.

The determination of the pre-ejection period provides an indicator which is suitable for the diagnosis and monitoring of cardiac insufficiency. Furthermore, in the variation in which the system comprises at least one telemetry module, a warning message can be transmitted to care personnel when the analysis module detects an abnormal increase in the duration of the pre-ejection period over time, which could be an indication of cardiac insufficiency.

Thus, the present system is suitable for evaluating and optimizing a cardiac resynchronization therapy where the objective is to reduce the pre-ejection period without modifying the left ventricular ejection time.

What is claimed is:

1. An implantable medical system for measuring at least one physiological parameter, the system comprising:
    a first implantable medical device provided with a dipole transmitter, the dipole transmitter being formed of two electrodes connected to a generator and being configured to transmit an electrical signal;
    a second implantable medical device distinct from the first implantable medical device and provided with a dipole receiver, the dipole receiver being formed of two additional electrodes, each one being distinct from the electrodes of the dipole transmitter, the dipole receiver being configured to collect the electrical signal transmitted by means of the dipole transmitter;
    a detector configured to capture an electrocardiogram or an electrogram of a patient's heart;
    an analysis module comprising at least one amplifier, an envelope detector, an analogue-to-digital converter, and a processor configured to:
        process the electrical signal captured by the dipole receiver;
        compare and correlate the processed electrical signal to an acoustic signal representative of sounds of the patient's heart; and
        associate the correlated electrical signal and the electrocardiogram or the electrogram to determine therefrom a parameter representative of a pre-ejection period.

2. The system of claim 1, wherein the analysis module is further configured to extract, from the processed electrical signal, at least one of a variation in volume or a variation in pressure as a function of time proportional to a drop in voltage between the dipole transmitter and the dipole receiver.

3. The system of claim 1, wherein the determination of the pre-ejection parameter includes combining an R wave or a Q wave of a QRS complex captured by the detector.

4. The system of claim 1, wherein the analysis module is further configured to monitor a second parameter representative of an efficacy of a therapy based on the pre-ejection parameter representative of the pre-ejection period.

5. The system of claim 1, wherein the two additional electrodes of the dipole receiver are configured to simultaneously capture the electrical signal emitted by the at least one dipole emitter and at least one of the electrocardiogram or the electrogram.

6. The system of claim 1, wherein the analysis module is activated based on detection of at least one peak of a PQRST complex captured by the detector.

7. The system of claim 1, wherein:
    one of the first implantable medical device or the second implantable medical device is a subcutaneous implantable cardioverter defibrillator or an event recorder; and the other of the first implantable medical device or the second implantable medical device is an implantable endocardial device.

8. The system of claim 7, wherein the implantable endocardial device is a leadless cardiac pacemaker.

* * * * *